(12) United States Patent
Gevgilili et al.

(10) Patent No.: US 11,666,521 B2
(45) Date of Patent: Jun. 6, 2023

(54) CONDITIONING COMPOSITIONS CONTAINING CATIONIC COMPOUNDS, A SILANE COMPOUND AND SILICA PARTICLES AND METHODS FOR USE

(71) Applicant: L'OREAL, Paris (FR)

(72) Inventors: Halil Gevgilili, Weehawken, NJ (US); Jun Liang, Staten Island, NY (US)

(73) Assignee: L'OREAL, Paris (FR)

( * ) Notice: Subject to any disclaimer, the term of this patent is extended or adjusted under 35 U.S.C. 154(b) by 527 days.

(21) Appl. No.: 16/216,471

(22) Filed: Dec. 11, 2018

(65) Prior Publication Data

US 2020/0179257 A1 Jun. 11, 2020

(51) Int. Cl.
| | |
|---|---|
| *A61Q 5/12* | (2006.01) |
| *A61K 8/58* | (2006.01) |
| *A61K 8/898* | (2006.01) |
| *A61Q 5/02* | (2006.01) |
| *A61K 8/02* | (2006.01) |
| *A61K 8/42* | (2006.01) |
| *A61K 8/34* | (2006.01) |
| *A61K 8/365* | (2006.01) |
| *A61K 8/25* | (2006.01) |

(52) U.S. Cl.
CPC ............ *A61K 8/585* (2013.01); *A61K 8/0241* (2013.01); *A61K 8/25* (2013.01); *A61K 8/342* (2013.01); *A61K 8/365* (2013.01); *A61K 8/42* (2013.01); *A61K 8/898* (2013.01); *A61Q 5/02* (2013.01); *A61Q 5/12* (2013.01); *A61K 2800/805* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 4,185,087 A | 1/1980 | Morlino | |
| 7,470,725 B2 | 12/2008 | Schwertfeger et al. | |
| 2003/0095944 A1 | 5/2003 | Midha | |
| 2009/0293899 A1 | 12/2009 | Woodland et al. | |
| 2011/0155163 A1 | 6/2011 | Viravau et al. | |
| 2011/0158927 A1 | 6/2011 | Viravau et al. | |
| 2011/0182842 A1 | 7/2011 | Aires et al. | |
| 2012/0093754 A1* | 4/2012 | Molenda ............... | A61K 8/898 424/70.9 |
| 2012/0125914 A1* | 5/2012 | Yue ........................ | H05B 3/34 219/548 |
| 2013/0011360 A1 | 1/2013 | Viravau et al. | |
| 2013/0309282 A1 | 11/2013 | Takehana | |
| 2015/0118270 A1 | 4/2015 | Lorant et al. | |
| 2015/0320656 A1 | 11/2015 | Khenniche et al. | |
| 2017/0135943 A1* | 5/2017 | Puls ....................... | A61K 8/39 |
| 2017/0151157 A1* | 6/2017 | Gevgilili ............... | A61K 8/8182 |
| 2017/0281522 A1* | 10/2017 | Gevgilili ............... | A61K 8/342 |

FOREIGN PATENT DOCUMENTS

| | | |
|---|---|---|
| FR | 2989888 A1 | 11/2013 |
| JP | 2012163798 A1 | 8/2012 |

* cited by examiner

*Primary Examiner* — Jyothsna A Venkat
(74) *Attorney, Agent, or Firm* — Polsinelli PC

(57) ABSTRACT

Disclosed are compositions for treating and conditioning keratinous substrates, comprising a silane compound; hydrophobic silica aerogel particles; a first organic acid; a cationic surfactant chosen from fatty dialkylamines; a second organic acid; a fatty alcohol; water; and optionally, a silicone compound other than the silane compound. Also disclosed are methods for treating and conditioning keratinous substrates using the composition.

3 Claims, No Drawings

CONDITIONING COMPOSITIONS CONTAINING CATIONIC COMPOUNDS, A SILANE COMPOUND AND SILICA PARTICLES AND METHODS FOR USE

FIELD OF THE INVENTION

The present application relates to cosmetic compositions for use on keratinous substrates, such as hair. In particular, it relates to compositions and methods for treating and conditioning hair.

BACKGROUND

Certain hair types are naturally thin and/or fine. In addition, any type of hair can diminish in quality and/or quantity over time by age and/or due to factors such as natural greasiness, sweat, shredded skin cells from the scalp, pollution, and dirt. These factors can result in thinning hair and/or harm the visual appearance and the feel of the hair, and lead to lank body and decreased volume. The magnitude of the consequences of these factors, which are almost all inevitable, is variable, depending on, for example, the quality of the hair, length, style, and environmental factors.

Hair care products are used to combat these drawbacks. Conventional cleansing compositions such as shampoos, for example, which contain surfactants such as anionic, nonionic and/or amphoteric type surfactants, can be employed to remove the diverse types of soils typically present on the substrate such as hair.

These cleansing compositions, while providing good cleansing power, may yield poor intrinsic cosmetic properties due to the fact that the nature of such a cleansing treatment may result in a less conditioned or rough feel to the hair due to, for example, the gradual removal of the natural or applied fats, lipids, or proteins contained in or at the surface of the hair. Such cleansing treatments may also result in tangling of hair fibers or less manageablility to the hair. It is thus desirable for manufacturers of personal care products to create formulations that can be used alone or in conjunction with hair cleansing products that would help address the problems. These formulations can be in the form of rinse-off or leave-in compositions such as conditioners and masques.

A hair conditioner is generally a rinse-off product which can be used on hair after it has been shampooed and rinsed. Aside from the conditioning properties that it may impart to hair, manufacturers also desire to design conditioners that can confer other cosmetic benefits such as those provided by hair styling products, for example leave-in gel and mousse compositions that impart volume and body while they are on the hair. Some leave-in styling products use polymers, for example film-forming polymers, to provide volumizing properties. However, some of the ingredients in styling compositions that provide the styling properties can be easily removed from the hair, for example by rinsing or washing. Thus, any cosmetic benefits to the hair from such products are generally diminished or removed once the hair is rinsed or washed. It is thus one objective of the invention to create a hair conditioning composition that provides additional benefits to hair such as volumizing and bodifying effects even after rinsing off the composition from the hair and that can last over a period of time.

BRIEF SUMMARY

The instant disclosure relates to compositions that provide conditioning properties to keratinous substrates, such as keratin fibers, in particular hair, and at the same time, provide mass, volume or body to the hair wherein such effects can be long-lasting, that is, the effect remains even after repeated washings or cleansing using the compositions of the present disclosure. The disclosure also relates to a hair conditioning process using the compositions of the instant disclosure.

Thus, the present disclosure relates to a composition for treating keratinous substrates, the composition containing:
(a) at least one silane compound corresponding to formula (I):

$$R_1Si(OR_2)_z(R_3)_x(OH)_y \qquad (I)$$

in which:
$R_1$ is a cyclic or acyclic, linear or branched, saturated or unsaturated $C_1$-$C_{22}$, in particular C2-C20, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group;
it being possible for R1 to be interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3;
(b) at least one hydrophobic silica aerogel particle;
(c) first organic acid;
(d) at least one cationic surfactant chosen from fatty dialkylamines;
(e) a second organic acid;
(f) at least one fatty alcohol; and
(g) water.

The disclosure also relates to a composition for treating keratinous substrates, the composition containing:
(a) a first phase comprising:
(i) a pre-formed silane-silica mixture comprising:
(1) at least one silane compound corresponding to formula (I):

$$R_1Si(OR_2)_z(R_3)_x(OH)_y \qquad (I)$$

in which:
$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3;

(2) at least one hydrophobic silica aerogel particle;
(ii) a first organic acid; and
(iii) water; and
   (b) a second phase comprising:
      (i) at least one cationic surfactant chosen from fatty dialkylamines;
      (ii) a second organic acid;
      (iii) at least one fatty alcohol; and
      (iv) water;

The above-described first phase and the second phase are combinable to form a single phase.

The composition of the disclosure optionally contain at least one silicone other than the at least one silane compound.

Embodiments of the disclosure also relate to a process for conditioning a keratinous substrate, such as hair and/or the scalp, involving applying the above-described composition onto the keratinous substrate, and to methods of imparting or increasing the volume or mass or body of the keratinous substrate, such as hair, by treating or contacting the hair with the above-described compositions.

The compositions of embodiments of the disclosure are stable over time and do not undergo phase separation. In addition, the compositions are creamy in appearance.

The compositions of the instant disclosure are stable, and can deliver conditioning, softness and detangling properties to hair as well as mass, body, and/or volume to hair that can be long-lasting (over at least 8 hours). Hair treated and/or contacted with the compositions according to embodiments of the disclosure can provide mass, body, volume, a fuller appearance, conditioning, and ease of combing/detangling while wet.

It is to be understood that both the foregoing general description and the following detailed description are exemplary and explanatory only, and are not restrictive of the disclosure.

Other subjects, characteristics, aspects and advantages of embodiments of the disclosure will emerge even more clearly on reading the description and the various examples that follow.

DETAILED DESCRIPTION

As used herein, the expression "at least one" means one or more and thus includes individual components as well as mixtures/combinations.

In the present patent application, a species is termed as being "cationic" when it bears at least one permanent positive charge or when it can be ionized as a positively charged species, under the conditions of use of the compositions of embodiments of the disclosure (for example the medium or the pH) and not comprising any anionic filler.

A species is termed as being "nonionic" when it is neither cationic nor anionic within the meaning of the disclosure, in particular when it comprises no cationic or anionic groups within the meaning of the disclosure.

A species is termed as being "anionic" when it bears at least one permanent negative charge or when it can be ionized as a negatively charged species, under the conditions of use of the compositions of embodiments of the disclosure (for example the medium or the pH) and not comprising any cationic filler.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

The term "comprising" (and its grammatical variations) as used herein is used in the inclusive sense of "having" or "including" or "containing" and not in the exclusive sense of "consisting only of".

"Keratinous substrates" as used herein, includes, but is not limited to keratin fibers such as hair on the human head and hair comprising eyelashes. "Keratinous substrates" as used herein, may also refer to the skin such as lips, finger nails or toe nails, and the scalp.

As used herein, the terms "applying a composition onto "keratinous substrates" as used herein, includes, and "applying a composition onto "keratinous substrates" or "keratin fibers" such as hair on a human head with at least one of the compositions of the disclosure, in any manner.

As used herein, "formed from," means obtained from chemical reaction of, wherein "chemical reaction," includes spontaneous chemical reactions and induced chemical reactions. As used herein, the phrase "formed from," is open ended and does not limit the components of the composition to those listed.

As used herein, the term "pre-formed" or variations thereof as used in conjunction with the silane-silica mixture of the instant disclosure means obtained from the combination of the at least one silane compound and the at least one hydrophobic silica aerogel particle resulting in a silane-silica mixture before any other ingredient or compound is combined with the silane compound and/or the hydrophobic silica aerogel particle.

The term "stable" as used herein means that the composition does not exhibit phase separation and/or crystallization.

The term "treat" (and its grammatical variations) as used herein refers to the application of the compositions of the present disclosure onto keratinous substrates such as hair. The term "treat" (and its grammatical variations) as used herein also refers to contacting keratinous substrates such as hair with the compositions of the present disclosure onto "Volatile", as used herein, means having a flash point of less than about 100° C.

"Non-volatile", as used herein, means having a flash point of greater than about 100° C.

"Substituted" as used herein, means comprising at least one substituent. Non-limiting examples of substituents include atoms, such as oxygen atoms and nitrogen atoms, as well as functional groups, such as acyloxyalky groups, carboxylic acid groups, amine or amino groups, acylamino groups, amide groups, halogen containing groups, ester groups, thiol groups, sulphonate groups, thiosulphate groups, siloxane groups, and polysiloxane groups. The substituent(s) may be further substituted.

The terms "organic compound" and "having an organic structure" mean compounds containing carbon atoms and hydrogen atoms and optionally heteroatoms such as S, O, N or P, alone or in combination.

The term "polymer" is understood to mean, within the meaning of the disclosure, a compound characterized by the multiple repetition of one or more species of atoms or groups of atoms, known as monomers, linked to each other in amounts sufficient to provide a set of properties that do not vary markedly with the addition or removal of one or a few of the monomers.

The term "film-forming polymer" is understood to mean a polymer which is capable of forming, by itself alone or in the presence of an additional film-forming agent, a macroscopically continuous or semi-continuous film on a support, in particular on keratinous substances, such as a cohesive film.

The term "rinse-off" is used herein to mean that a keratinous substrate such as hair is rinsed and/or washed with water either after or during the application of a composition onto the keratinous substrate, and before drying and/or styling said keratinous substrate. At least a portion of the composition is removed from the keratinous substrate during the rinsing and/or washing. A "rinse-off" product refers to a composition such as a hair care composition that is rinsed and/or washed with water either after or during the application of the composition onto the keratinous substrate, and before drying and/or further processing/treating/styling said keratinous substrate.

The compositions and methods of the present disclosure can comprise, consist of, or consist essentially of the essential elements and limitations of the disclosure described herein, as well as any additional or optional ingredients, components, or limitations described herein or otherwise useful.

An embodiment of the present disclosure is directed to a composition for treating keratinous substrates, the composition containing:

(a) at least one silane compound corresponding to formula (I):

$$R_1Si(OR_2)_z(R_3)_x(OH)_y \quad (I)$$

in which:

$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3;

(b) at least one hydrophobic silica aerogel particle;

(c) first organic acid;

(d) at least one cationic surfactant chosen from fatty dialkylamines;

(e) a second organic acid;

(f) at least one fatty alcohol; and (g) water;

wherein the at least one silane compound and the at least one hydrophobic silica aerogel particle comprise a pre-formed silane-silica mixture; and wherein the composition comprises a first phase containing the pre-formed silane-silica mixture, the first organic acid, and water; and a second phase containing the at least one cationic surfactant chosen from fatty dialkylamines, the second organic acid, the at least one fatty alcohol, and water.

In another embodiment, the disclosure also relates to a composition for treating keratinous substrates, the composition containing:

(a) a first phase comprising:
(i) a pre-formed silane-silica mixture comprising:
(1) at least one silane compound corresponding to formula (I):

$$R_1Si(OR_2)_z(R_3)_x(OH)_y \quad (I)$$

in which:

$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO), $R_2$ and $R_3$, which may be identical or different, represent a linear or branched alkyl group comprising from 1 to 6 carbon atoms, y denotes an integer ranging from 0 to 3, and z denotes an integer ranging from 0 to 3, and x denotes an integer ranging from 0 to 2, with z+x+y=3;

(2) at least one hydrophobic silica aerogel particle;

(ii) a first organic acid; and (iii) water; and (b) a second phase comprising:
(i) at least one cationic surfactant chosen from fatty dialkylamines;
(ii) a second organic acid;
(iii) at least one fatty alcohol; and
(iv) water;

wherein the first phase and the second phase form a single phase in the composition.

In one embodiment, the at least one silane compound is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane, their oligomers, and mixtures thereof.

In one embodiment, the at least one silane compound of formula (I) is chosen from 3-aminopropyltriethoxysilane, oligomers thereof, and mixtures thereof.

In one embodiment, the amount of the at least one silane compound ranges from about 0.05% to about 5% by weight, based on the total weight of the composition, including all ranges and subranges therebetween.

In one embodiment, the at least one hydrophobic silica aerogel particle includes silica silylate.

In one embodiment, the amount of the at least one hydrophobic silica aerogel particle ranges from about 0.01% to about 1% by weight, based on the total weight of the composition, including all ranges and subranges therebetween.

In one embodiment, the pre-formed silane-silica mixture (also referred to herein as "pre-mix") is in the form of a gel or a powder.

In one embodiment, the amount of the at least one silane is compound is greater than the amount of the at least one hydrophobic silica aerogel particle, i.e., the weight ratio of the silane compound to the hydrophobic silica aerogel particle ("silane to silica" ratio) in the pre-formed silane-silica mixture or in the composition of the invention can range from about 9 to about 2, or such as from about 8.5 to about 3, or such as from about 8 to about 4, and preferably from about 7.8 to about 4.5, including all ranges and subranges therebetween.

In one embodiment, the weight ratio of the silane compound to the hydrophobic silica aerogel particle ("silane to silica" ratio) in the pre-formed silane-silica mixture or in the composition of the invention can range from about 9 to about 0.1, or such as from about 8.5 to about 0.3, or such as from about 8 to about 0.4, or such as from about 7.8 to about 0.5, or such as from about 2 to about 0.6, or such as from about 1 to about 0.6, including all ranges and subranges therebetween.

In one embodiment, the first organic acid and the second organic acid in the compositions of the instant disclosure are chosen from mono-carboxylic acids and polycarboxylic acids (with 2 or more carboxylic acid groups).

In one embodiment, the first organic acid is chosen from lactic acid.

In one embodiment, the at least one silane compound of formula (I) is 3-aminopropyltriethoxysilane (APTES) and the first organic acid is lactic acid and the ratio by weight of the at least one silane compound to acid in the compositions of the invention ranges from about 3 to about 0.3, or about 2.5 to about 0.4, or about 2.2 to about 0.5, including all ranges and subranges therebetween, or is at about 0.5, 0.57, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3.(our very original inventions that were moved were 7.7, we probably don't need to include it, since it is covered in 0045, in previous edit max was 9).

In one embodiment, the at least one cationic surfactant includes a dimethylamine derivative.

In one embodiment, the dimethylamine derivative is chosen from stearyl dimethyl amine, stearamidopropyl dimethylamine, brassicamidopropyl dimethylamine, and mixtures thereof.

In one embodiment, the at least one cationic surfactant is stearamidopropyl dimethylamine.

In one embodiment, the amount of the at least one cationic surfactant ranges from about 0.1% to about 15% by weight, based on the total weight of the composition, including all ranges and subranges therebetween.

In one embodiment, the second organic acid is chosen from tartaric acid.

In one embodiment, the at least one cationic surfactant is stearamidopropyl dimethylamine and the second organic acid is tartaric acid and the ratio by weight of the at least one cationic surfactant to acid in the compositions of the invention ranges from about 10 to about 2, or about 8 to about 3, or about 7.5 to about 3.5, or about 7.1 to about 4, including all ranges and subranges therebetween, or is at about 2, 2.5, 3, 3.5, 4, 4.5, 4.6, 4.7, 4.8, 4.9, 5, 5.1, 5.2, 5.3, 5.4, 5.5, 6, 6.1, 6.2, 6.3, 6.4, 6.5, 6.6, 6.7, 6.8, 6.9, 7, 7.5, 8, 8.5, 9, 9.5, or 10.

In one embodiment, the first organic acid and the second organic acid are used in amounts such that either or both of the respective phases above (first and second phases) and/or the final composition achieves a pH ranging from about 3 to about 6, and preferably from about 3.5 to about 4.5, including all ranges and subranges therebetween.

In one embodiment of the present disclosure, when the first organic acid is lactic acid and the second organic acid is tartaric acid, each acid is present in an amount such that the pH of the composition ranges from about 3.5 to about 4.5, including all ranges and subranges therebetween.

In one embodiment, the total amount of the first organic acid and the second organic acid ranges from about 0.03% to about 3% by weight, based on the total weight of the composition, including all ranges and subranges therebetween.

In one embodiment, the at least one fatty alcohol is chosen from at least one non-alkoxylated, saturated or unsaturated, linear or branched fatty alcohol having from 6 to 60 carbon atoms.

In one embodiment, the amount of the at least one fatty alcohol ranges from about 1% to about 15% by weight, based on the total weight of the composition, including all ranges and subranges therebetween.

In one embodiment, the at least one fatty alcohol is chosen from cetearyl alcohol (a mixture of two fatty alcohols, cetyl alcohol and stearyl alcohol).

In one embodiment, the at least one fatty alcohol comprises cetyl alcohol and cetearyl alcohol.

In one embodiment, the at least one fatty alcohol comprises cetyl alcohol and stearyl alcohol.

In one embodiment, the at least one fatty alcohol is chosen from cetyl alcohol, stearyl alcohol, cetearyl alcohol, and mixtures thereof.

In one embodiment, the present disclosure is directed to a composition for providing to hair one or more of the following effects of conditioning, manageability, volumizing, mass, body, and shape, the composition comprising:
(a) from about 0.06% to about 0.9% by weight of at least one silane compound corresponding to formula (I):

$$R_1Si(OR_2)_z(R_3)_x(OH)_y \qquad (I)$$

in which:
R$_1$ is a cyclic or acyclic, linear or branched, saturated or unsaturated C$_1$-C$_{22}$, in particular C$_2$-C$_{20}$, hydrocarbon-based chain, which may be substituted with a group chosen from amine groups NH$_2$ or NHR (R being a linear or branched C$_1$-C$_{20}$, in particular C$_1$-C$_6$, alkyl, a C$_3$-C$_{40}$ cycloalkyl or a C$_6$-C$_{30}$ aromatic radical); the hydroxyl group (OH), a thiol group, an aryl group (more particularly benzyl), which is possibly substituted with an NH$_2$ or NHR group; it being possible for R1 to be interrupted with a heteroatom (O, S or NH) or a carbonyl group (CO),
R$_2$ and R$_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3;
(b) from 0.05% to about 1% by weight of at least one hydrophobic silica aerogel particle;
(c) first organic acid chosen from tartaric acid, lactic acid, malic acid, maleic acid, oxalic acid, malonic acid, citric acid, aspartic acid, salicylic acid, benzoic acid, acetic acid, formic acid, and mixtures thereof, and preferably chosen from lactic acid;
(d) from about 0.5% to about 4% by weight of at least one cationic surfactant chosen from fatty dialkylamines;
(e) a second organic acid chosen from tartaric acid, lactic acid, malic acid, maleic acid, oxalic acid, malonic acid, citric acid, aspartic acid, salicylic acid, benzoic acid, acetic acid, formic acid, and mixtures thereof, and preferably chosen from tartaric acid;

(f) from about 3.5% to about 6% by weight of at least one fatty alcohol;
(g) water; and
(h) optionally, at least one silicone other than the at least one silane compound.

In one embodiment, the composition of the disclosure for treating keratinous substrates such as hair contains:
(a) a first phase comprising:
  (i) a pre-formed silane-silica mixture comprising:
    (1) from about 0.15% to about 2% by weight of at least one silane compound corresponding to formula (I):

in which:
$R_1$ is a cyclic or acyclic, linear or branched, saturated or unsaturated $C_1$-$C_{22}$, in particular C2-C20, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3; and
    (2) from about 0.05% to about 1% by weight of at least one hydrophobic silica aerogel particle;
  (ii) a first organic acid chosen from tartaric acid, lactic acid, malic acid, maleic acid, oxalic acid, malonic acid, citric acid, aspartic acid, salicylic acid, benzoic acid, acetic acid, formic acid, and mixtures thereof, and preferably chosen from lactic acid; and
  (iii) water; and
(b) a second phase comprising:
  (i) from about 0.1% to about 3% by weight of at least one cationic surfactant chosen from fatty dialkylamines;
  (ii) a second organic acid chosen from tartaric acid, lactic acid, malic acid, maleic acid, oxalic acid, malonic acid, citric acid, aspartic acid, salicylic acid, benzoic acid, acetic acid, formic acid, and mixtures thereof, and preferably chosen from tartaric acid;
  (iii) from about 3% to about 6% by weight of at least one fatty alcohol chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, and mixtures thereof;
  (iv) water, and
  (v) optionally, at least one silicone other than the at least one silane compound;
all weights being based on the total weight of the composition.

In one embodiment, the present disclosure is directed to a composition for providing to hair one or more of the following effects of conditioning, manageability, volumizing, mass, body, and shape, the composition comprising:
(a) a first phase comprising:
  (i.) a pre-formed silane-silica mixture comprising:
    (1) from about 0.15% to about 0.9% by weight of at least one silane compound chosen from 3-aminopropyltriethoxysilane (APTES); and
    (2) from about 0.065% to about 1% by weight, or from about 0.065% to about 0.5% by weight, or from about 0.2% to about 1% by weight of at least one hydrophobic silica aerogel particle;
  (ii) a first organic acid chosen from lactic acid; and
  (iii) water;
wherein the weight ratio of the at least one silane compound to the at least one hydrophobic silica aerogel particle in the pre-formed silane-silica mixture or in the composition ranges from about 9 to about 0.1;
wherein the weight ratio of the at least one silane compound to first organic acid in the composition ranges from about 2 to about 0.5; and
(b) a second phase comprising:
  (i) from about 0.5% to about 4% by weight of at least one cationic surfactant chosen from stearamidopropyl dimethylamine;
  (ii) a second organic acid chosen from tartaric acid;
  (iii) from about 3% to about 6% by weight of at least one fatty alcohol chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, and mixtures thereof;
  (iv) water; and
  (v) optionally, at least one silicone other than the at least one silane compound;
wherein the weight ratio of the at least one cationic surfactant to the second organic acid ranges from about 7 to about 4;
wherein the pH of the composition is from about 3.5 to about 4.5;
all weights being based on the total weight of the composition; and The first phase and the second phase in any one of the above-described compositions are form a single phase or are combinable to form a single phase.

In some embodiments, the above-described compositions of the present disclosure further comprise at least one silicone compound other than the at least one silane compound of formula (I).

In one embodiment, the at least one silicone other than the at least one silane compound is chosen from dimethicones, dimethicone copolymers, amino functional silicones, and mixtures thereof.

In one embodiment, the amino functional silicones comprise at least one primary, secondary or tertiary amine or a quaternary ammonium group.

In one embodiment, the at least one silicone compound is provided or added to the compositions of the invention as a mixture comprising at least one surfactant such as alkoxylated fatty alcohols, fatty alcohols, and mixtures thereof.

In one embodiment, the at least one silicone compound is not in an emulsion form.

In one embodiment, the compositions of the instant disclosure may comprise a cationic surfactant comprising alkyl quaternary ammonium compounds chosen from behentrimonium chloride, cetrimonium chloride, quaternium-22, behenylamidopropyl-2, 3-di-hydroxypropyldimethylammonium chloride, palmitylamidopropyltrimethylammonium chloride, and chloride and methyl sulfate of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, distearyldimethylammonium chloride, oleocetyldimethylhydroxyethylammonium chloride, stearamidopropyldimethyl (myristyl acetate) ammonium chloride, di(C1-C2 alkyl) (C12-C22 alkyl)hydroxy(C1-C2alkyl)ammonium salt, or alkyltrimethylammonium salt in which the alkyl radical comprises 12 to 24 carbon atoms, propanetallowdiammonium dichloride, behentrimonium methosulfate, quaternium-83, quaternium-87, and mixtures thereof.

In one embodiment, the amount of the cationic surfactant comprising alkyl quaternary ammonium compounds ranges from about 0.1% to about 10% by weight, based on the total weight of the composition, including all ranges and subranges therebetween.

In one embodiment, the keratinous substrates include hair.

In one embodiment, the above-described compositions of the instant disclosure are rinse-off conditioning compositions.

In one embodiment of the instant disclosure, a method for treating and/or conditioning and/or imparting volume and/or body and/or mass to a keratinous substrate, comprises contacting the keratinous substrate such as hair with the above-described compositions of the invention.

In one embodiment, the method comprises a step of leaving the compositions of the instant disclosure on the keratinous substrate for a leave-on time and followed by a step of rinsing the keratinous substrate with water.

In one embodiment, the composition of the present disclosure is capable of being applied onto the keratinous substrates following the application of a shampoo or a cleansing or a detergent-based composition onto the keratinous substrates.

The compositions according to various embodiments of the disclosure have a homogenous texture, i.e., not lumpy, and are easy to apply and spread on the hair.

In one embodiment of the instant disclosure, a method of making the compositions of the present disclosure comprises: pre-mixing the at least one silane compound and the least one hydrophobic silica aerogel particle in order to form a pre-formed silane-silica mixture; combining the pre-formed silane-silica mixture with a first organic acid and water in order to form a first phase; and combining the first phase with a second phase containing at least one cationic surfactant chosen from fatty dialkylamines; a second organic acid; at least one fatty alcohol; and water to form the final composition.

The weight ratio of the at least one silane compound to the least one hydrophobic silica aerogel particle in the pre-formed silane-silica mixture or in the composition comprising the first and second phases may be varied, depending on the formulation processing and scale up methods employed. Generally, hydrophobic silica particles do not easily disperse in water and without the use of high speed homogenization, the direct addition of such particles to water aqueous systems result in particles floating to the top of the composition. The inventors have unexpectedly and surprisingly discovered that when the hydrophobic silica aerogel particles of the instant disclosure are first combined with the silane compound (for example, APTES) to form a powder or gel, the formation of the silane-silica mixture ("pre-mix" or "pre-formed") facilitates the incorporation or dispersion of the hydrophobic silica particles into the rest of the composition and better or much improved processing with respect to scale-up and industrialization.

Without being bound to any one theory, the inventors of the present invention believe that pre-mixing the silane with the hydrophobic silica aerogel particles to form a pre-formed silane-silica mixture increases the hydrophilicity of the silica aerogel particles such that the particles can be more easily incorporated into an aqueous system while maintaining its hydrophobic properties. The presence of amino functionality on the silane also introduces cationic charges to aerogel (silica) particles providing them with greater affinity to the hair's surface which is anionically charged.

It has been surprisingly and unexpectedly discovered that the compositions according to the disclosure are stable over time, exhibit no visible phase separation, and allow retention of the cosmetic effects of its ingredients such as the cationic surfactant chosen from fatty dialkylamines (preferably, neutralized fatty dialkylamines), the silane compound, hydrophobic silica aerogel particles, the fatty alcohols, and silicone compounds and/or other cationic surfactants (when present) such that hair can be effectively or satisfactorily volumized and easy to detangle and comb through after treatment with the composition. It is possible that the volumizing effect imparted to the hair remains even after several washings of the hair.

Without being bound to any one theory, the inventors of the present invention also believe that maintaining the hydrophobic nature of the silica aerogel particles by pre-forming a silane-silica mixture (pre-mix) can result in instant and longer lasting volumizing effects to hair after the compositions are rinsed-off from the hair as well as control the sebum or oil on the scalp and/or hair.

Silane Compound

According to the invention, the composition comprises at least one silane compound corresponding to formula (I) and/or its oligomers and/or polymers thereof.

Formula (I) is as follows:

$$R_1Si(OR_2)_z(R_3)_x(OH)_y \qquad (I)$$

in which:
$R_1$ is a cyclic or acyclic, linear or branched, saturated or unsaturated $C_1$-$C_{22}$, in particular $C_2$-$C_{20}$, hydrocarbon-based chain, which may be substituted with a group chosen from amine groups $NH_2$ or NHR (R being a linear or branched $C_1$-$C_{20}$, in particular $C_1$-$C_6$, alkyl, a $C_3$-$C_{40}$ cycloalkyl or a $C_6$-$C_{30}$ aromatic radical); the hydroxyl group (OH), a thiol group, an aryl group (more particularly benzyl), which is possibly substituted with an $NH_2$ or NHR group; it being possible for R1 to be interrupted with a heteroatom (O, S or NH) or a carbonyl group (CO),
$R_2$ and $R_3$, which may be identical or different, represent a linear or branched alkyl group comprising from 1 to 6 carbon atoms,
y denotes an integer ranging from 0 to 3, and
z denotes an integer ranging from 0 to 3, and
x denotes an integer ranging from 0 to 2, with z+x+y=3.

Preferably, $R_1$ is a linear or branched, preferably linear, saturated $C_1$-$C_{22}$, in particular $C_2$-$C_{12}$, hydrocarbon-based chain, which may be substituted with an amine group $NH_2$ or NHR (R=$C_1$-$C_{20}$, in particular $C_1$-$C_6$, alkyl).

Preferably, $R_2$ represents an alkyl group comprising from 1 to 4 carbon atoms, better still a linear alkyl group comprising from 1 to 4 carbon atoms, and preferably the ethyl group.

Preferably, z ranges from 1 to 3.
Preferably, y=0.
Preferentially, z=3, and therefore x=y=0.

In one embodiment of the invention, $R_1$ represents a linear alkyl group comprising from 7 to 18 carbon atoms and more particularly from 7 to 12 carbon atoms, or a $C_1$-$C_6$, preferably $C_2$-$C_4$, aminoalkyl group. More particularly, $R_1$ represents an octyl group.

In one embodiment of the invention, $R_1$ is a linear or branched, saturated or unsaturated $C_1$-$C_{22}$ hydrocarbon-based chain, substituted with an amine group $NH_2$ or NHR (R=$C_1$-$C_{20}$, in particular $C_1$-$C_6$, alkyl, $C_3$-$C_{40}$ cycloalkyl or $C_6$-$C_{30}$ aromatic). In this variant, $R_1$ preferably represents a $C_1$-$C_6$, preferably $C_2$-$C_4$, aminoalkyl group.

Preferably, the first silane compound of the present invention is an alkoxysilane.

Preferably, the composition comprises at least one compound of formula (Ib) chosen from alkoxysilanes such as 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane, N-(2-aminoethylaminomethyl)phenethyltrimethoxysilane, and mixtures thereof.

In certain embodiments, the siliane of the disclosure is an alkoxysilane selected from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane or oligomers thereof, and mixtures thereof.

In preferred embodiments, the silane compound of the present invention is chosen from 3-aminopropyltriethoxysilane (APTES) or oligomers thereof, or mixtures thereof.

The silane compound used in the composition of the invention, in particular those comprising a basic function, may be partially or totally neutralised. In particular, the neutralising agent may be chosen from organic or inorganic acids, such as citric acid, tartaric acid, lactic acid or hydrochloric acid, preferably, lactic acid.

Preferably, the optionally neutralised silanes according to the invention are water-soluble and in particular soluble at a concentration of 2%, better still at a concentration of 5% and even better still at a concentration of 10% by weight in water at a temperature of 25° C. and at atmospheric pressure (1 atm). The term "soluble" is intended to mean the formation of a single macroscopic phase.

The silane(s) of formula (I) and/or oligomers and/or polymers thereof may be present in the composition according to the invention in an amount of about 0.05% to about 5% by weight, such as from about 0.06% to about 4% by weight, from about 0.1% to about 4% by weight, from about 0.15% to about 3% by weight, from about 0.2% to about 2% by weight, from about 0.2% to about 2% by weight, from about 0.2% to about 1%, or from about 0.2% to less than 1%, such as from about 0.2% to about 0.8%, by weight of active material, based on the total weight of the composition, including all ranges and subranges therebetween.

In certain embodiments, the silane(s) of formula (I) and/or oligomers and polymers thereof may be present in the composition according to the invention in an amount of about 0.05% to about 5% by weight, such as from about 0.06% to about 3% by weight, from about 0.06% to about 1% by weight, or from about 0.06% to about 0.9% by weight of active material, based on the total weight of the composition, including all ranges and subranges therebetween.

In various embodiments, the total amount of the silane(s) of formula (I) is about 0.05%, 0.06%, 0.075%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.25%, 1.5%, 1.75%, 2%, 2.25%, 2.5%, 2.75%, 3%, 3.5%, 4%, 4.5%, 5% by weight of active material, based on the total weight of the composition.

Hydrophobic Silica Aerogel Particle

The compositions of the present disclosure comprise at least one hydrophobic silica aerogel particle.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid shrinkage of the pores and of the material.

The hydrophobic silica aerogel particles used in the present invention exhibit a specific surface area per unit of mass (SM) ranging from 500 to 1500 m²/g, preferably from 600 to 1200 m²/g and better still from 600 to 800 m²/g, and a size, expressed as the volume-mean diameter (D[0.5]), ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size, expressed as the volume-mean diameter (D[0.5]), ranging from 1 to 30 µm, preferably from 5 to 25 µm, better still from 5 to 20 µm and even better still from 5 to 15 µm.

The specific surface area per unit of mass can be determined by the nitrogen absorption method, known as the BET (Brunauer-Emmett-Teller) method. The BET specific surface area corresponds to the total specific surface area of the particles under consideration.

The sizes of the silica aerogel particles can be measured by static light scattering using a commercial particle size analyser of MasterSizer 2000 type from Malvern.

According to one advantageous embodiment, the hydrophobic silica aerogel particles used in the present invention have a specific surface area per unit of mass (SM) ranging from 600 to 800 m²/g and a size expressed as the volume-mean diameter (D[0.5]) ranging from 5 to 20 µm and even better still from 5 to 15 µm.

The silica aerogel particles used in the present invention may advantageously have a tapped density ρ ranging from 0.02 g/cm³ to 0.10 g/cm³, or such as from 0.03 g/cm³ to 0.10 g/cm³, preferably from 0.04 g/cm³ to 0.10 g/cm³, or preferably from 0.05 g/cm³ to 0.08 g/cm³.

In the context of the present invention, this density ρ known as the tapped density, may be assessed according to the following protocol:

40 g of powder are poured into a measuring cylinder; the measuring cylinder is then placed on a Stay 2003 machine from Stampf Volumeter; the measuring cylinder is then subjected to a series of 2500 packing motions (this operation is repeated until the difference in volume between two consecutive tests is less than 2 percent); the final volume Vf of packed powder is then measured directly on the measuring cylinder. The tapped density is determined by the ratio w/Vf, in this instance 40/Vf (Vf being expressed in cm³ and w in g).

According to one preferred embodiment, the hydrophobic silica aerogel particles used in the present invention have a specific surface area per unit of volume SV ranging from 5 to 100 m²/cm³, such as from 10 to 90 m²/cm³ or from 15 to 40 m²/cm³, preferably from 20 to 85 m²/cm³, more preferably from 24 to 80 m²/cm³.

The specific surface area per unit of volume is given by the relationship: $S_V = S_M \times \rho$, where ρ is the tapped density, expressed in g/cm³, and $S_M$ is the specific surface area per unit of weight, expressed in m²/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method of determination of oil uptake of a powder described in the standard NF T 30-022. It corresponds to the amount of oil adsorbed onto the available surface of the powder and/or absorbed by the powder by measurement of the wet point, described below:

An amount m=2 g of powder is placed on a glass plate and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at the rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The aerogels used according to the present invention are hydrophobic silica aerogels, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles modified at the surface by silylation, reference may be made to the document U.S. Pat. No. 7,470,725.

Use will preferably be made of hydrophobic silica aerogel particles surface-modified with trimethylsilyl groups.

Mention may be made, as hydrophobic silica aerogels which can be used in the invention, for example, of the aerogel sold under the name VM-2260 (INCI name: Silica silylate) by Dow Corning, the particles of which have a mean size of approximately 1000 microns and a specific surface area per unit of mass ranging from 600 to 800 $m^2/g$.

Mention may also be made of the aerogels sold by Cabot under the references AEROGEL TLD 201, AEROGEL OGD 201, AEROGEL TLD 203, ENOVA AEROGEL MT 1100 and ENOVA AEROGEL MT 1200.

Use will be made more particularly of the aerogel sold under the name VM-2270 (INCI name: Silica silylate), by the company Dow Corning, the particles of which have an average size ranging from 5-15 microns and a specific surface area per unit of mass ranging from 600 to 800 $m^2/g$.

In some embodiments, the hydrophobic silica aerogel particles are present in the composition according to the invention in an active material content ranging from about 0.01% to about 1% by weight, or such as from about 0.02% to about 0.8% by weight, or such as from about 0.025% to about 0.5% by weight, or such as from about 0.03% to about 0.4% by weight, or such as from about 0.04% to about 0.3% by weight, or such as from about 0.04% to about 0.2% by weight, or such as from about 0.05% to about 0.1% by weight, or such as from about 0.06% to about 0.1% by weight, based on the total weight of the composition, including all ranges and subranges therebetween.

In certain embodiments, the hydrophobic silica aerogel particles may be present in a total amount of about 0.01%, 0.02%, 0.03%, 0.04%, 0.045%, 0.05%, 0.0525%, 0.055%, 0.0575%, 0.06%, 0.0625%, 0.065%, 0.0675%, 0.07%, 0.0725%, 0.075%, 0.0775%, 0.08%, 0.0825%, 0.085%, 0.0875%, 0.09%, 0.0925%, 0.095%, 0.0975%, 0.1%, 0.125%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.525%, 0.55%, 0.575%, 0.6%, 0.625%, 0.65%, 0.675%, 0.5%, 0.725%, 0.75%, 0.775%, 0.8%, 0.8255, 0.75%, 0/875%, 0.9%, 0.925%, 0.95%, 0.975%, or 1%, by weight, based on the total weight of the composition.

Silane-Silica Mixture

The at least one silane compound and the at least one hydrophobic silica aerogel particle of the present disclosure may be combined separately from other components of the compositions of the present disclosure ("pre-mixed") in order to form a silane-silica mixture ("pre-mix" or "pre-formed" silane-silica mixture).

In one embodiment, the amount of the at least one silane compound is greater than the amount of the least one hydrophobic silica aerogel particle in the pre-formed silane-silica mixture.

In one embodiment, the amount of the at least one silane compound is less than the amount of the least one hydrophobic silica aerogel particle in the pre-formed silane-silica mixture.

In one embodiment, the amount of the at least one silane is compound is greater than the amount of the at least one hydrophobic silica aerogel particle, i.e., the weight ratio of the silane compound to the hydrophobic silica aerogel particle ("silane to silica" ratio) in the pre-formed silane-silica mixture or in the composition of the invention can range from about 9 to about 2, or such as from about 8.5 to about 3, or such as from about 8 to about 4, and preferably from about 7.8 to about 4.5, including all ranges and subranges therebetween. In one embodiment, the weight ratio of the silane compound to the hydrophobic silica aerogel particle ("silane to silica" ratio) in the pre-formed silane-silica mixture or in the composition of the invention can range from about 9 to about 0.1, or such as from about 8.5 to about 0.3, or such as from about 8 to about 0.4, or such as from about 7.8 to about 0.5, or such as from about 2 to about 0.6, or such as from about 1 to about 0.6, including all ranges and subranges therebetween.

In various embodiments, the weight ratio of the silane compound to the hydrophobic silica aerogel particle ("silane to silica" ratio) in the pre-formed silane-silica mixture or in the composition of the invention is about 0.25, 0.3, 0.35, 0.4, 0.45, 0.5, 0.6, 0.65, 0.68, 0.7, 0.75, 0.8, 0.85, 0.9, 0.95, 1, 1.1, 1.2, 1.25, 1.3, 1.4, 1.5, 1.6, 1.75, 1.8, 1.9, 2, 2.2, 2.5, 2.8, 3, 3.2, 3.5, 3.8, 4, 4.2, 4.5, 4.8, 5, 5.2, 5.5, 5.8, 6, 6.2, 6.5, 6.8, 7, 7.2, 7.5, 7.7, 7.8, 8, 8.2, 8.5, 8.7, 9.

In one embodiment, the pre-formed silane-silica mixture is in the form of a gel.

In one embodiment, the pre-formed silane-silica mixture is in the form of a powder.

In one embodiment, the pre-formed silane-silica mixture is in the form of a gel-powder.

Organic Acid

The first and second organic acids in the compositions of the present invention are chosen from mono-carboxylic acids and polycarboxylic acids (with 2 or more carboxylic acid groups such as di- and/or tri-carboxylic acids).

Suitable examples of the first and second organic acids of the present invention include acetic acid, terephthalic acid, HOOC-PEG-COOH acid; citric acid, tartaric acid; betaine hydrochloride, gluconic acid or 2-ethylcaproic acid, lactic acid, salicylic acid, glycolic acid, malic acid, maleic acid, oxalic acid, malonic acid, aspartic acid, glutamic acid, benzoic acid, acetic acid, formic acid, and mixtures thereof.

Other suitable examples of the first and second organic acids are chosen from polycarboxylic acids selected from aspartic acid, glutamic acid, oxalic acid, succinic acid, tartaric acid, mucic acid, citric acid, malic acid, maleic acid, phthalic acid, poly(ethylene glycol) bis(carboxymethyl)ethers, acrylic polyacid, copolymer of acrylic acid and maleic acid, polyaspartic acid, carboxylic polydimethylsiloxanes, and mixtures thereof.

In other embodiments, the first organic acid and/or the second organic acid is a sulfonic acid selected from benzene sulfonic acid, sulfonic acid HSO2OH, taurine, 2-[4-(2-hydroxy-ethyl)-piperazin-1-yl]ethane sulfonic acid (or HEPES), and (3E)-3-(4-{(E)-[7,7-dimethyl-3-oxo-4-(sulfomethyl)bicyclo[2.2.1]hept-2-ylidene]methyl}benzylidene)-7,7-dimethyl-2- oxobicyclo[2.2.1]hept-1- yl]methane sulfonic acid, and mixtures thereof.

In an embodiment, the first organic acid and/or the second organic acid is selected from trichloroacetic acid, L-poly (ethylene glycol) bis(carboxymethyl)ether having a molecular weight of 250 g/mol, salicylic acid derivatives, jasmonic acid derivative, 3-hydroxy-2-pentyl-cyclopentyl acetic acid, 2-[4-(2-hydroxy-ethyl)-piperazin-1-yl]-ethanesulfonic acid, pyruvic acid, mandelic acid, and mixtures thereof.

In an embodiment, the first organic acid and/or the second organic acid is selected from tartaric acid, lactic acid, malic acid, maleic acid, oxalic acid, malonic acid, citric acid, aspartic acid, salicylic acid, benzoic acid, acetic acid, formic acid and mixtures thereof.

In some cases, the first organic acid and/or the second organic acid comprise at least one di-carboyxlic acid. Non-limiting examples include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and mixtures thereof. In some cases, tartaric acid is preferred, especially when the fatty dialkylamine is a fatty dimethylamine, such as stearamidopropyl dimethylamine.

In an embodiment, the first organic acid is utilized to neutralize or decrease the pH of the silane-silica mixture in water.

In some embodiments, the second organic acid is utilized (either in its total amount or a portion of its total amount) to "neutralize" the at least one cationic surfactant chosen from fatty dialkylamines so that the fatty dialkylamines can be combined with fatty alcohols to form a stable composition. After neutralization with an organic acid, the fatty dialkylamine compounds exhibit a cationic charge and therefore have properties similar to a cationic surfactant. This allows the fatty dialkylamine compounds to provide conditioning and discipline benefits to the hair.

The total amount of the second organic acid may vary but is typically in an amount sufficient to neutralize the at least one cationic surfactant chosen from fatty dialkylamines.

In an embodiment, the first organic acid comprises lactic acid.

In an embodiment, the second organic acid comprises tartaric acid.

In an embodiment, the compositions of the present invention comprise lactic acid and tartaric acid.

The first organic acid and the second organic acid may be present in a total amount of from about 0.03% to about 3% by weight, such as from about 0.04% to about 2.5% by weight, or such as from about 0.05% to about 2% by weight, or such as from about 0.06% to about 1.5% by weight or such as from about 0.08% to about 1%, based on the total weight of the composition, including all ranges and subranges therebetween.

In certain embodiments, the first organic acid and the second organic acid may be present in a total amount of about 0.03%, 0.05%, 0.08%, 0.1%, 0.125%, 0.15%, 0.175%, 0.2%, 0.225%, 0.25%, 0.275%, 0.3%, 0.325%, 0.35%, 0.375%, 0.4%, 0.425%, 0.45%, 0.475%, 0.5%, 0.525%, 0.55%, 0.575%, 0.6%, 0.625%, 0.65%, 0.675%, 0.5%, 0.725%, 0.75%, 0.775%, 0.8%, 0.8255, 0.75%, 0/875%, 0.9%, 0.925%, 0.95%, 0.975%, 1%, 1.2%, 1.4%, 1.5%, 1.6%, 1.8%, 2%. 2.2%, 2.4%, 2.6%, 2.8%, or 3% by weight, based on the total weight of the composition.

In other embodiments, the first organic acid and/or the second organic acid are employed in amounts sufficient to neutralize the at least one silane compound and/or the at least one cationic surfactant chosen from fatty dialkylamines and/or to achieve the desired pH of the first phase and/or the second phase and/or the compositions of the present disclosure.

Cationic Surfactant

The composition of the invention comprises at least one cationic surfactant chosen from fatty dialkylamines. In some instances, the fatty dialkylamines correspond to the compounds of formula:

$$RN(R')_2 \qquad (A)$$

wherein R is a fatty group containing at least 6 carbon atoms (and up to 30 carbon atoms) In addition, R can be linear or branched, saturated or unsaturated, and substituted or unsubstituted. Typically, R is a linear or branched, acyclic alkyl or alkenyl group; and the groups R', which may be identical or different, represent a hydrocarbon radical containing less than 6 carbon atoms. In addition, the groups R', which may be identical or different, are linear or branched, saturated or unsaturated, and substituted or unsubstituted. Preferably, the groups R' are methyl groups. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, stearyl dimethyl amine, and mixtures thereof.

In some instances, the fatty dialkylamines relate to fatty amidoamine compounds corresponding to compounds of the following formula and their salts:

$$RCONHR''N(R')_2 \qquad (B)$$

wherein R is a fatty group containing at least 6 carbon atoms (and up to 30 carbon atoms). In addition, R can be linear or branched, saturated or unsaturated, and substituted or unsubstituted. Typically, R is a linear or branched, acyclic alkyl or alkenyl group; R" is a divalent hydrocarbon radical containing less than 6 carbon atoms, preferably 2 or 3 carbon atoms, and the groups R', which may be identical or different, represent a hydrocarbon radical containing less than 6 carbon atoms. In addition, the groups R', which may be identical or different, are linear or branched, saturated or unsaturated, substituted or unsubstituted. Preferably, the groups R' are methyl groups. Non-limiting examples include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, stearyl dimethyl amine, brassicamidopropyl dimethylamine, and mixtures thereof.

In an embodiment the at least one cationic surfactant chosen from fatty dialkylamines is selected from stearamidopropyl dimethylamine which may be commercially available under the tradename MACKINE 301, from Rhodia.

The total amount of the at least one cationic surfactant chosen from fatty dialkylamines may vary but is typically about 0.1% to about 15% by weight, based on the total weight of the composition of the present invention. In some cases, the total amount of the at least one cationic surfactant chosen from fatty dialkylamines is about 0.1% to about 12% by weight, about 0.1% to about 10% by weight, about 0.1% to about 8% by weight, about 0.1% to about 6% by weight, about 0.1% to about 4% by weight, about 0.1% to about 3% by weight, or about 0.5% to about 2.5% by weight, based on the total weight of the composition, including all ranges and subranges therebetween.

In various embodiments, the total amount of the at least one cationic surfactant chosen from fatty dialkylamines is about 0.1%, 0.125%, 0.15%, 0.175%, 0.2%, 0.25%, 0.3%, 0.33%, 0.35%, 0.375%, 0.4%, 0.425%, 0.45%, 0.475%, 0.5%, 0.525%, 0.55%, 0.575%, 0.6%, 0.625%, 0.65%, 0.675%, 0.7%, 0.725%, 0.75%, 0.775%, 0.8%, 0.825%, 0.83%, 0.85%, 0.875%, 0.9%, 0.925%, 0.95%, 0.975%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, or 5%, by weight, based on the total weight of the composition of the present invention.

Fatty Alcohol

The compositions of the present disclosure comprise at least one fatty alcohol. The fatty alcohols that may be used in the composition of the disclosure include, but are not limited to, non-alkoxylated, saturated or unsaturated, linear or branched, and have from 6 to 60 carbon atoms, such as from 8 to 30 carbon atoms.

The fatty alcohols of the present disclosure are chosen from solid and liquid fatty alcohols.

The saturated liquid fatty alcohols can be branched. They can optionally comprise, in their structure, at least one aromatic or non-aromatic ring. They can be acyclic.

The unsaturated liquid fatty alcohols exhibit, in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

Liquid fatty alcohols may be selected, for example, from octyldodecanol, 2-butyloctanol, 2-hexyldecanol, 2-undecylpentadecanol, oleyl alcohol or linoleyl alcohol, isostearyl alcohol, and mixtures thereof.

Solid fatty alcohols may be crystalline, amorphous or pasty. The solid fatty alcohols of the present invention are solid at room temperature (25 degrees centigrade) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight.

In an embodiment, the solid fatty alcohols preferably have a melting point of greater than or equal to 28° C. and have a viscosity, at a temperature of 40 ° C. and at a shear rate of 1 $s^{-1}$, of greater than or equal to 1 Pa.s.

In an embodiment, the melting point of the fatty alcohols ranges from 30° C. to 250° C., such as from 32° C. to 150° C. or such as from 35° C. to 150° C.

The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 6 to 60 carbon atoms, such as from 10 to 50 carbon atoms, or such as from 12 to 24 carbon atoms.

The solid fatty alcohols preferably have the structure of formula: R—OH in which R especially denotes a C6-C60, for example, C8-C60, preferably C10-C50 or even C12-C30 alkyl group, R possibly being substituted with one or more hydroxyl groups, R possibly being branched. The solid fatty alcohols of the invention may be non-oxyalkylenated and/or non-glycerolated. These fatty alcohols may be constituents of animal or plant waxes.

The solid fatty alcohol may represent a mixture of fatty alcohols, which means that several species of fatty alcohol may coexist, in the form of a mixture, in a commercial product. One example of such a commercial product is cetearyl alcohol, a mixture of cetyl alcohol and stearyl alcohol, commercially available under the trade name of LANETTE O OR from the company BASF. Cetyl alcohol may also be commercially available under the tradename of LANETTE 16 from the company BASF.

In an embodiment, the solid fatty alcohols of the present invention may be chosen from myristyl alcohol, cetyl alcohol, stearyl alcohol, cetearyl alcohol, and mixtures thereof, octyldodecanol, 2-butyloctanol, 2-hexyldecanol, 2-undecylpentadecanol, oleic alcohol, linoleic alcohol, behenyl alcohol, and mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

In an embodiment of the present invention, the fatty alcohol is chosen from non-alkoxylated, saturated or unsaturated, linear or branched fatty alcohol having from 6 to 60 carbon atoms is chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, behenyl alcohol, 2-dodecylhexadecanol, 2-tetradecyl-1-octadecanol, 2-tetradecyl-1-eicosanol, 2-hexadecyl-1-octadecanol and 2-hexadecyl-1-eicosanol, octyldodecanol, 2-butyloctanol, 2-hexyldecanol, 2-undecylpentadecanol, oleyl alcohol or linoleyl alcohol, isostearyl alcohol, and mixtures thereof.

In an embodiment of the present invention, the fatty alcohol is chosen from cetyl alcohol.

In an embodiment of the present invention, the fatty alcohol is chosen from cetearyl alcohol.

In an embodiment of the present invention, the fatty alcohol comprises cetyl alcohol and cetearyl alcohol.

In an embodiment of the present invention, the fatty alcohol comprises cetyl alcohol and stearyl alcohol.

In an embodiment of the present invention, the fatty alcohol is chosen from cetyl alcohol, stearyl alcohol, cetearyl alcohol, and mixtures thereof.

In an embodiment, the fatty alcohols of the present invention are chosen from liquid fatty alcohol, solid fatty alcohols, and mixtures thereof.

The fatty alcohol(s) may be present in the composition according to the invention in an amount of from about 1% to about 15% by weight, such as from about 1.5% to about 14% by weight, from about 2% to about 12% by weight, from about 2.5% to about 10% by weight, from about 3% to about 8%, or from about 3% to about 6% by weight of active material, based on the total weight of the composition, including all ranges and subranges therebetween In various embodiments, the total amount of the fatty alcohol(s) is about 1%, 1.25%, 1.5%, 1.6%, 1.75%, 2%, 2.25%, 2.75%, 2.8%, 2.9%, 3%, 3.2%, 3.5%, 3.6%, 3.8%, 4%, 4.25%, 4.4%, 4.5%, 4.6%, 4.75, 5%, 5.5%, 6%, 6.5%, 7%, 7.5%, 8% by weight of active material, based on the total weight of the composition.

Water

The compositions according to various embodiments of the disclosure may be aqueous. Water can be present in total amounts of about 95% or less, such as from about 95% to about 5% by weight, or about 90%, 80%, 70%, 60%, 50%, 40%, 30%, 20%, 10%, or 5% or less, by weight, based on the total weight of the composition. In further embodiments, water can be present in an amount of about 95%, such as about 90%, 80%, 70%, 60%, 50%, 40%, 30%, 20%, 10%, or 5%, by weight, based on the total weight of the composition, including all ranges and subranges therebetween. Additionally, water can be present in the compositions of the present disclosure in the amount of from about 20% to about 95% by weight, from about 40% to about 90% by weight, or from about 50% to about 80% by weight, based on the total weight of the compositions.

In other embodiments, water can be present in the compositions of the present disclosure in the amount of at least about 95%, 90%, 80%, 70%, 60%, 50%, 45%, 40%, 30%, 20%, 10%, 5% by weight, based on the total weight of the compositions.

Silicone Compound

The compositions of the present disclosure may further comprise at least one silicone compound other than the silane compound (b). The at least one silicone compound may be chosen from dimethicone, dimethicone copolymers, amino functional silicones, and mixtures thereof.

In an embodiment, the at least one silicone compound of the present disclosure is amino functional silicone.

In an embodiment, the at least one silicone compound of the present disclosure is amino functional silicone comprising at least one functionalized amodimethicone.

The term "amino functional silicone" as used herein can mean any silicone comprising at least one primary, secondary or tertiary amine or a quaternary ammonium group (i.e., a quaternized group).

As amino functional silicone that may be used in the scope of the instant disclosure, the following can be cited:

a) polysiloxanes corresponding to formula (A):

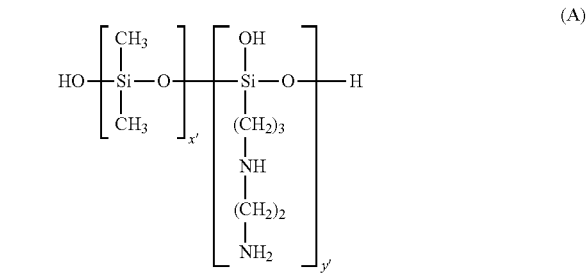

in which x' and y' are integers such that the weight-average molecular weight (Mw) is comprised between about 5000 and 500 000;

b) amino silicones corresponding to formula (B):

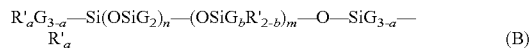

in which:

G, which may be identical or different, designate a hydrogen atom, or a phenyl, OH or $C_1$-$C_8$ alkyl group, for example methyl, or $C_1$-$C_8$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula —$C_qH_{2q}L$ in which q is a number ranging from 2 to 8 and L is an optionally quaternized amino group chosen from the following groups:

—NR"-Q-N(R")$_2$

—N(R")$_2$

—N+(R")$_3$A-

—N+H(R")$_2$A-

—N+H$_2$(R") A-

—N(R")-Q-N+R"H$_2$ A-

—NR"-Q-N+(R")$_2$H A-

—NR"-Q-N+(R")$_3$ A-, in which R″, which may be identical or different, denote hydrogen, phenyl, benzyl, or a saturated monovalent hydrocarbon-based radical, for example a $C_1$-$C_{20}$ alkyl radical; Q denotes a linear or branched $CrH_{2r}$ group, r being an integer ranging from 2 to 6, preferably from 2 to 4; and A- represents a cosmetically acceptable ion, in particular a halide such as fluoride, chloride, bromide or iodide.

A group of amino silicones corresponding to this definition (B) is represented by the silicones called "trimethylsilylamodimethicone" having formula (C):

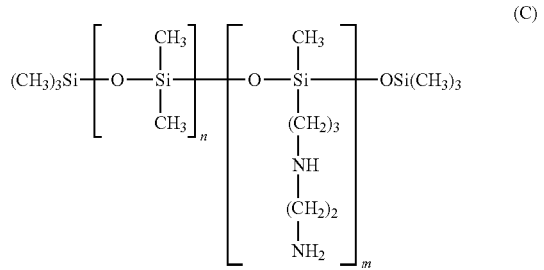

in which n and m have the meanings given above, in formula B.

Another group of amino silicones corresponding to this definition is represented by silicones having the following formulae (D) or (E):

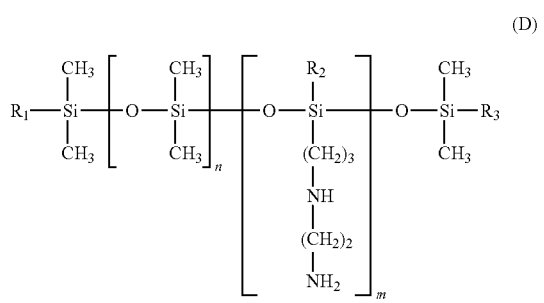

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

$R_1$, $R_2$, $R_3$, which may be identical or different, represent a hydroxy or $C_1$-$C_4$ alkoxy radical, where at least one of the radicals $R_1$ to $R_3$ denotes an alkoxy radical.

The alkoxy radical is preferably a methoxy radical.

The hydroxy/alkoxy mole ratio ranges preferably from 0.2:1 to 0.4:1 and preferably from 0.25:1 to 0.35:1 and more particularly equals 0.3:1.

The weight-average molecular weight (Mw) of the silicone ranges preferably from 2000 to 1 000 000, more particularly from 3500 to 200 000.

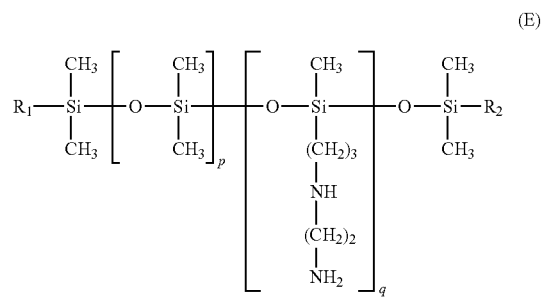

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

$R_1$, $R_2$, which are different, represent a hydroxy or $C_1$-$C_4$ alkoxy radical, where at least one of the radicals $R_1$ or $R_2$ denotes an alkoxy radical.

The alkoxy radical is preferably a methoxy radical.

The hydroxy/alkoxy mole ratio ranges generally from 1:0.8 to 1:1.1 and preferably from 1:0.9 to 1:1 and more particularly equals 1:0.95.

The weight-average molecular weight (Mw) of the silicone ranges preferably from 2000 to 200 000, even more particularly 5000 to 100 000 and more particularly from 10 000 to 50 000.

Commercial products corresponding to these silicones having structure (D) or (E) may include in their composition one or more other amino silicones whose structure is different than formulae (D) or (E).

A product containing amino silicones having structure (D) is sold by Wacker under the name Belsil® ADM 652.

A product containing amino silicones having structure (E) is sold by Wacker under the name Fluid WR 1300®.

When amino functional silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-average size of the silicone particles in the emulsion generally ranges from 3 nm to 500 nanometres. Preferably, in particular as amino silicones having formula (E), microemulsions are used whose average particle size ranges from 5 nm to 60 nanometres (limits included) and more preferably from 10 nm to 50 nanometres (limits included). Accordingly, according to the invention the microemulsions of amino silicone having formula (E) sold as Finish CT 96 E® or SLM 28020® by Wacker can be used.

Another group of amino silicones corresponding to this definition is represented by the following formula (F):

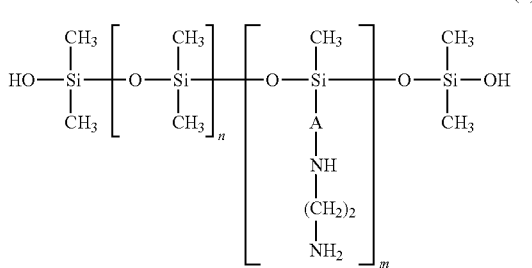

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;
A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1 000 000 and even more particularly from 3500 to 200 000.

A preferred silicone of formula (F) is amodimethicone (INCI name) sold under the tradename XIAMETER® MEM-8299 Cationic Emulsion by Dow Corning or sold under the tradename SILSOFT 253, by Momentive Performance Materials.

Another group of amino silicones corresponding to this definition is represented by the following formula (G):

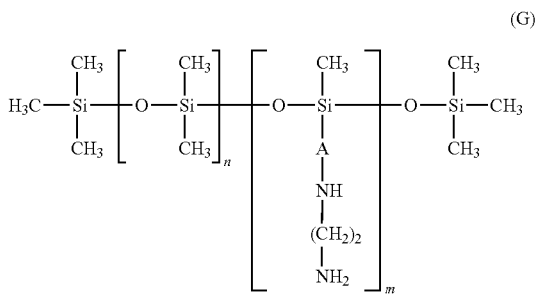

in which:
m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1 000 000 and even more particularly from 1000 to 200 000.

A silicone having this formula is for example DC2-8566 Amino Fluid by Dow Corning.

c) amino silicones corresponding to formula (H):

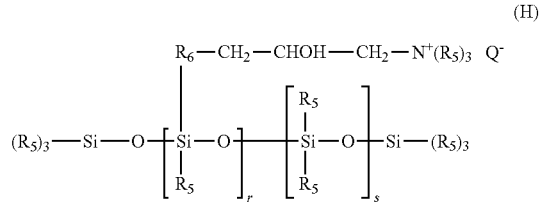

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in patent U.S. Pat. No. 4,185,087.

d) quaternary ammonium silicones having formula (I):

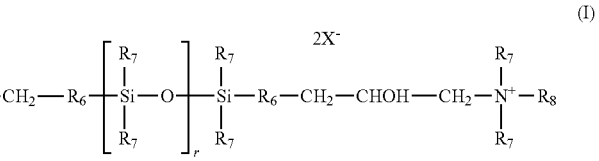

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NH-$COR_7$ radical;

X- is an anion such as a halide ion, in particular chloride, or an organic acid salt (for example acetate);

r represents a mean statistical value from 2 to 200 and in particular from 5 to 100;

These silicones are described, for example, in patent application EP-A 0 530 974.

e) amino silicones having formula (J):

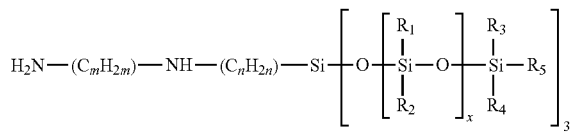

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

f) multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

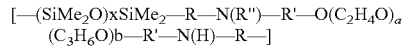

or alternatively

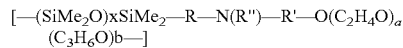

in which:

a is an integer greater than or equal to 1, preferably ranging from 5 to 200, more particularly ranging from 10 to 100;

b is an integer comprised between 0 and 200, preferably ranging from 4 to 100, more particularly between 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably comprised between 5000 and 1 000 000, more particularly between 10 000 and 200 000.

Mention may be made especially of the silicones sold under the names SILSOFT A-843 or SILSOFT A+ by Momentive.

g) the alkylamino silicones corresponding to formula (K) below:

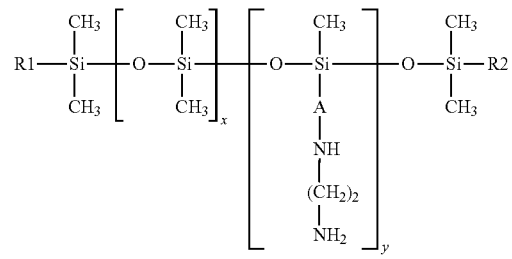

in which:

x and y are numbers ranging from 1 to 5000; preferably, x ranges from 10 to 2000 and especially from 100 to 1000; preferably, y ranges from 1 to 100;

$R_1$ and $R_2$, which may be identical or different, preferably identical, are linear or branched, saturated or unsaturated alkyl radicals, comprising 6 to 30 carbon atoms, preferably 8 to 24 carbon atoms and especially 12 to 20 carbon atoms;

A denotes a linear or branched alkylene radical containing from 2 to 8 carbon atoms, Preferably, A comprises 3 to 6 carbon atoms, especially 4 carbon atoms; preferably, A is branched. Mention may be made especially of the following divalent radicals: —$CH_2CH_2CH_2$ and —$CH_2CH(CH_3)CH_2$—.

Preferably, $R_1$ and $R_2$, which may be identical or different, are saturated linear alkyl radicals comprising 6 to 30 carbon atoms, preferably 8 to 24 carbon atoms and especially 12 to 20 carbon atoms; mention may be made in particular of dodecyl, tetradecyl, pentadecyl, hexadecyl, heptadecyl, octadecyl, nonadecyl and eicosyl radicals; and preferentially, $R_1$ and $R_2$, which may be identical or different, are chosen from hexadecyl (cetyl) and octadecyl (stearyl) radicals.

Preferentially, the silicone is of formula (K) with:

x ranging from 10 to 2000 and especially from 100 to 1000;

y ranging from 1 to 100;

A comprising 3 to 6 carbon atoms and especially 4 carbon atoms; preferably, A is branched; and more particularly A is chosen from the following divalent radicals: CH$_2$CH$_2$CH$_2$ and —CH$_2$CH(CH$_3$)CH$_2$—; and R$_1$ and R$_2$, which may be identical or different, being linear, saturated alkyl radicals comprising 6 to 30 carbon atoms, preferably 8 to 24 carbon atoms and especially 12 to 20 carbon atoms; chosen in particular from dodecyl, tetradecyl, pentadecyl, hexadecyl, heptadecyl, octadecyl, nonadecyl and eicosyl radicals; preferentially, R$_1$ and R$_2$, which may be identical or different, being chosen from hexadecyl (cetyl) and octadecyl (stearyl) radicals.

A preferred amino silicone of formula (K) is bis-cetearylamodimethicone (INCI name).

Mention may be made especially of the silicone sold under the name SILSOFT AX by Momentive.

h) silicone compounds with at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Most preferred are quaternium 80, silicone quaternium-16, silicone quaternium-18, silicone quaternium-15, and mixtures thereof.

The silicone compounds with at least one quaternary ammonium group can also include those compounds of formula (B) when L in formula (B) is a quaternized amino group as described.

The silicone compound of the present disclosure may be provided or may be commercially available in emulsion form that further comprises surfactants chosen from nonionic surfactants, cationic surfactants, and mixtures thereof. In certain embodiments, the emulsion in which the silicone compound is contained is a microemulsion.

In some embodiments, the at least one silicone compound of the present disclosure is non amino functional silicone compound such as dimethicone copolymer such as a divinyldimethicone/dmimethicone copolymer, sold as DOW CORNING HMW 2220 NON-IONIC EMULSION by Dow Corning (in combination with C12-13 pareth-3 (and) C12-13 pareth-23) or dimethicone, sold as BELSIL DM 3800 E Wacker by Wacker.

In some embodiments, the at least one silicone compound of the present disclosure is an amino functional silicone compound such as amodimethicone or a functionalized amodimethicone such as bis(C13-15 alkoxy) PG amodimethicone, available under the tradename of DC 8500 or Dow Corning 8500 Conditioning Agent from Dow Corning.

The silicone compound(s) other the silane compound (b) may be present in the composition according to the invention in an amount of about 0.05% to about 5% by weight, such as from about 0.1% to about 4% by weight, from about 0.15% to about 3% by weight, from about 0.2% to about 3% by weight, or from about 0.3% to about 2.5%, by weight of the active material, based on the total weight of the composition, including all ranges and subranges therebetween.

In some embodiments, the silicone compound(s) may be introduced into the composition of the invention in the form of an emulsion material in an amount of about 0.05% to about 2% by weight, or from about 0.1% to about 1.5% by weight, or from about 0.1% to about 1% by weight, or from about 0.2% to about 0.9% by weight, or from about 0.4% to about 0.9%, by weight of active material, based on the total weight of the composition, including all ranges and subranges therebetween.

In some embodiments, the silicone compound(s) other the silane compound (b) may be introduced into the composition of the invention in the form of an emulsion material in an amount of about 0.05% to about 8% by weight, such as from about 0.1% to about 7% by weight, from about 0.15% to about 6% by weight, from about 0.2% to about 5% by weight, or from about 0.25% to about 4%, by weight, or from about 0.25% to about 2% by weight, of the active material, based on the total weight of the composition, including all ranges and subranges therebetween.

In various embodiments, the total amount of silicone compound(s) other the silane compound (b) is about 0.01%, 0.025%, 0.04%, 0.05%, 0.075%, 0.1%, 0.15%, 0.2%, 0.25%, 0.27%, 0.3%, 0.33%, 0.35%, 0.37%, 0.4%, 0.44%, 0.45%, 0.5%, 0.55%, 0.6%, 0.64%, 0.65%, 0.7%, 0.75%, 0.774%, 0.8%, 0.83%, 0.85%, 0.88%, 0.9%, 0.95%, 1%, 1.25%, 1.5%, 1.75%, 2%, 2.25% 2.5%, 2.75%, 3%, 3.25% 3.5%, 3.75%, or 4% by weight of the active material or the emulsion material, based on the total weight of the composition.

Cationic Surfactants Other than Fatty Dialkylamines

The compositions of the present disclosure may further comprise a second cationic surfactant other than fatty dialkylamines and may be chosen from alkyl quaternary ammonium or diammonium salts, and mixtures thereof.

Suitable examples of quaternary ammonium compounds are chosen from compounds, including their salts, of the general formula (C) below:

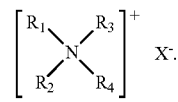

(C)

wherein R1, R2, R3, and R4, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamidoalkyl, hydroxyalkyl, aromatic, aryl or alkylaryl radical comprising from about 12 to about 30 carbon atoms, with at least one radical among R1, R2, R3 and R4 denoting a radical comprising from 8 to 30 carbon atom; and X"" is chosen from halides, phosphates, acetates, lactates, (C2-C6) alkyl sulfates, and alkyl- or alkylaryl-sulfonates.

The quaternary ammonium compound (C) may be selected from behenyltrimethylammonium chloride (also called behentrimonium chloride), cetyltrimethylammonium chloride (also called cetrimonium chloride), quaternium-22, behenylamidopropyl-2, 3-di-hydroxypropyldimethylammonium chloride, palmitylamidopropyltrimethylammonium chloride, and chloride and methyl sulfate of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, and mixtures thereof.

Other suitable examples of quaternary ammonium compounds include distearyldimethylammonium chloride, oleocetyldimethylhydroxyethylammonium chloride, stearamidopropyldimethyl (myristyl acetate) ammonium chloride, di(C1-C2 alkyl) (C12-C22 alkyl)hydroxy(C1-C2alkyl)ammonium salt, such as dialkyldimethylammonium or alkyltrimethylammonium salt in which the alkyl radical preferably comprises 12 to 24 carbon atoms, propanetallowdiammonium dichloride, behentrimonium methosulfate, and mixtures thereof.

Non-limiting examples of quaternary ammonium salts that comprise the first cationic surfactants of the present disclosure include in particular behentrimonium chloride, cetrimonium chloride, behentrimonium methosulfate, and mixtures thereof.

A preferred quaternary ammonium compound (C) is behentrimonium chloride (INCI name) sold under the tradename VARISOFT BT 85 by Evonik Goldschmidt.

In certain embodiments, the total amount of the second cationic surfactant ranges from about 0.1% to about 10% by weight, such as from about 0.2% to about 8% by weight, from about 0.5% to about 6% by weight, from about 0.6% to about 5% by weight, or from about 0.8% to about 3%, by weight of active material, based on the total weight of the composition of the present disclosure, including all ranges and subranges therebetween.

In various embodiments, the total amount of the second cationic surfactants is about 0.1%, 0.2%, 0.3%, 0.4%, 0.5%, 0.6%, 0.7%, 0.8%, 0.9%, 1%, 1.2%, 1.3%, 1.4%, 1.5%, 1.6%, 1.7%, 1.8%, 1.9%, 2%, 2.25%, 2.5%, 2.75%, 3%, 3.25%, 3.5%, 3.75%, 4%, 4.25%, 4.5%, 4.75%, 5%, 5.5%, 6%, 6.5%, 7%, 7.5%, 8%, 9%, and 10%, by weight of active material, based on the total weight of the composition of the present disclosure.

pH

The pH of the compositions according to the disclosure generally ranges from about 3 to about 6, for example, from about 3.0 to about 5.8, or from about 3.4 to about 5.5, or from about 3.5 to about 5.8, preferably from about 3.6 to about 5.5, and more preferably from about from about 3.8 to about 5.0 or such as from about 3.5 to about 4.5, including ranges and subranges therebetween. In certain embodiments, the pH of the compositions according to the disclosure is at about 3.0, 3.5, 3.6, 3.7, 3.8, 3.9, 4.0, 4.1, 4.2, 4.3, 4.4, 4.5, 4.6, 4.7, 4.8, 4.9, 5, 5.1, 5.2, 5.3, 5.4, or 5.5, and is preferably at about 3.5, 3.6, 3.7, 3.8, 3.9, 4.0, 4.1, 4.2, 4.3, 4.4 or 4.5.

Additional Components

The composition according to the disclosure may also comprise additional components chosen from cationic polymers, nonionic polymers, rheology modifiers, thickening and/or viscosity modifying agents, associative or non-associative polymeric thickeners, non-polymeric thickeners, non-polymeric surfactants (nonionic, cationic or amphoteric), nacreous agents, dyes or pigments, fragrances, mineral, plant or synthetic oils, waxes, vitamins, proteins including ceramides, vitamins, UV-screening agents, free-radical scavengers, antidandruff agents, hair-loss counteractants, hair restorers, preservatives, pH stabilizers, alkaline neutralizing agents, organic solvents (e.g., alcohols, polyols, silicone oils, and hydrocarbons), and mixtures thereof. A person skilled in the art will take care to select the optional additives and the amount thereof such that they do not harm the properties of the compositions of the present disclosure.

If present in the composition, these additional components are generally present in an amount ranging up to about 20% by weight of active material relative to the total weight of the composition, such as up to about 15%, up to about 12%, up to about 10%, up to about 8%, up to about 5%, such as from 0% to 20% by weight, based on the total weight of the compositions of the instant disclosure.

The compositions of certain embodiments may comprise stabilizers, for example sodium chloride, magnesium dichloride or magnesium sulfate.

The rheology modifiers and thickening/viscosity-modifying agents that may be employed in compositions of the present disclosure may include any water-soluble or water-dispersible compound that is compatible with the compositions of the disclosure, such as acrylic polymers, non-acrylic polymers, starch, cellulose-based polymers, non-polymeric and polymeric gelling agents, and mixtures thereof.

In an embodiment, the compositions of the present disclosure is provided as part of a multi-component hair cosmetic agent for treating hair, the hair cosmetic agent comprising:
  a) a first component comprising a shampoo or a cleansing or a detergent-based composition; and
  b) a second component comprising the conditioning composition of the disclosure comprising at least one silane compound of formula (I), at least one hydrophobic silica aerogel particles, a first organic acid; a cationic surfactant chosen from fatty dialkylamines; a second organic acid; a least one fatty alcohol; and water;
wherein the first and second components are each packaged in a separate packaging assembly or container; and
wherein the first component is to be applied onto hair first followed by second component with an optional step of rinsing the hair with water in between the applications of the first and second components.

The first and second components may comprise a kit.

The compositions may be packaged in various forms, especially in bottles, in pump bottles or in tubes or in jars. The compositions may also impregnate applicators and articles, especially hair caps, gloves or wipes.

The compositions may be applied by hand, with an applicator nozzle, with a container equipped with a pump and a dispensing comb, or with an insoluble substrate or article impregnated with the composition.

Processes/Methods

The compositions according to the disclosure may be prepared according to the following general protocol (Protocol A):
1) The silane compound of formula (I) (e.g., APTES) is combined/blended with a hydrophobic silica aerogel particle (e.g., silica silylate as supplied by Dow Corning under the tradename DOW CORNING VM-2270 AEROGEL FINE PARTICLES) in a side kettle resulting in a silane-silica mixture ("pre-mix" or "pre-formed").

2) The pre-formed silane-silica mixture is dispersed in an organic acid solution (e.g., 5% lactic acid in water) to form a first phase.
3) In a main kettle, water is combined with a cationic surfactant chosen from fatty dialkyamines (e.g., stearamidopropyl dimethylamine).
4) The resulting mixture in the main kettle is heated to about 70° C. or higher and the pH is adjusted to 4.0 using an organic acid (e.g., tartaric acid).
5) Fatty alcohols are added to the main kettle, melted, then homogenized with the rest of the ingredients in the main kettle in order to form a second phase.
6) The second phase is cooled to a temperature ranging from about 45° C. to about 55° C., preferably to a temperature of about 50° C. Optional ingredients such as preservatives, fragrance, and silicones are added.
7) The second phase is cooled to about 35° C. and below.
8) The first phase in the side kettle is added into the main kettle and combined with the second phase in order to form the composition of the present disclosure.

Embodiments of the disclosure also relate to a process for treating keratinous materials, such as hair, which consists in applying an effective amount of a composition as defined above to the said keratinous materials, and in rinsing, for example with water, after an optional leave-on time.

Certain embodiments also relate to a process for conditioning keratinous materials, which consists in applying an effective amount of a composition as defined above to the said keratinous materials, and in optionally rinsing, for example with water, after an optional leave-on time.

In some embodiments, keratinous materials, such as hair, may be washed or cleansed by a first step of applying a shampoo or cleansing or detergent-based composition, with an optional leave-on time, followed by a second step of applying the composition of the disclosure onto hair, with an optional step of rinsing the hair with water between the two first and second steps, and optionally rinsing the composition of the disclosure, for example with water, after an optional leave-on time.

The compositions may be applied to keratinous substrates, such as the hair, and subsequently rinsed off. In various embodiments, the compositions comprise hair care compositions for conditioning the hair, and in various embodiments the hair care composition will traditionally be rinsed off the hair within a short period of time after application to the hair, such as a period of time up to about 10 minutes, up to about 5 minutes, or up to about 2 minutes after application to the hair.

In various embodiments, processes according to the disclosure comprise applying the compositions described onto keratinous substrates, such as the hair, and subsequently rinsing the compositions off. The processes may, in various embodiments, impart conditioning and/or volume to the keratinous substrate to which the composition is applied, even after the composition is rinsed off. The processes may additionally impart long lasting volume as well as conditioning to the keratinous substrates.

As used herein, the method/process and composition disclosed herein may be used on the hair that has not been artificially dyed, pigmented or permed.

As used herein, the method/process and composition disclosed herein may be also used on the hair that has been artificially dyed, pigmented or permed.

EXAMPLES

The following Examples are intended to be non-restrictive and explanatory only, with the scope of the disclosure being defined by the claims.

The ingredient amounts in the compositions/formulas described below are expressed in % by weight, based on the total weight of the composition/formula.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective measurements. The following examples are intended to illustrate the disclosure without limiting the scope as a result.

Example 1: Compositions

TABLE 1

| Hair Conditioner Compositions (Inventive) | | | | |
|---|---|---|---|---|
| RAW MATERIALS/ INGREDIENTS US INCI NAME | Formula A | Formula B | Formula C | Formula D |
| | Amounts in % by weight | | | |
| STEARAMIDOPROPYL DIMETHYLAMINE | 2 | 2 | 2 | 2 |
| AMINOPROPYL TRIETHOXYSILANE (APTES) | 0.5 | 0.25 | 0.75 | 0.2 |
| SILICA SILYLATE$^a$ | 0.065 | 0.37 | 1 | 0.2 |
| FATTY ALCOHOLS (e.g., CETYL ALCOHOL, STEARYL ALCOHOL) | 4.6 | 4.6 | 4.6 | 4.6 |
| TARTARIC ACID | 0.42 | 0.42 | 0.42 | 0.42 |
| LACTIC ACID | 0.35 | 0.35 | 0.35 | 0.35 |
| SILICONES OTHER THAN APTES (BIS(C13-15 ALKOXY) PG-AMODIMETHICONE$^b$) | — | 0.27 | 0.83 | 0.33 |
| ADDITIVES, PRESERVATIVES, FRAGRANCE | 1.4 | 1.5 | 1.6 | 1.5 |
| WATER | QS 100 | QS 100 | QS 100 | QS 100 |
| RATIO OF APTES TO AEROGEL | 7.7 | 0.68 | 0.75 | 1 |

Designated ingredients in Table 1 are commercially available as:
$^a$HEXAMETHYLDISILOXANE TREATED SILICA GEL (FREE FLOWING POWDER), DOW CORNING VM-2270 AEROGEL FINE PARTICLES (Hydrophobic)
$^b$"Dow Corning 8500 Conditioning Agent"

The formulas above were prepared according to the following protocol (as based on general protocol A):
1) APTES (silane) and silica silylate (Aerogel) are pre-mixed in a side kettle to form a pre-formed silane-silica mixture or pre-mix.
2) The pre-formed silane-silica mixture is dispersed in water neutralized by lactic acid.
3) Water and stearamidopropyl dimethlyamine (fatty dialkyamine) are mixed in a main kettle.
4) The mixture is heated to about 70° C. and its pH is adjusted using tartaric acid.
5) The fatty alcohols are added into the main kettle, melted then homogenized into the rest of the mixture.
6) The mixture is cooled to about 50° C. and optional ingredients such as preservative, fragrance, and silicones (if present, as in Formula B, C or D) are added.
7) The mixture is cooled to about 35° C. and below and dispersed pre-mix or pre-formed silane-silica mixture in the side kettle is added into the main kettle.

The pH of the final formulas was within the range of 3.5 to 4.5. To achieve this pH range, the ratio by weight of APTES to lactic acid was in the range of from about 0.7 to about 2.14, and the ratio by weight of stearamidopropyl dimethyamine to tartaric acid was within the range of from about 4.8 to about 7.1.

The formulas of the invention were stable over time and did not undergo phase separation.

The stability protocol is as follows:
Under the conditions of 6 days Freeze/Thaw
Samples were put in 4° C., 25° C., and 45° C. chambers and monitored at 1 week, 4 weeks, and 8 weeks. Samples at 37° C. were monitored at 8 weeks.

Samples appear stable with pH and viscosity within specificatons.

Example 2: Comparative Commercial Product

TABLE 2

Comparative Hair Conditioner Formula Y
(advertised for its volumizing properties)
US INCI NAME WATER
STEARYL ALCOHOL
STEARAMIDOPROPYL DIMETHYLAMINE
CETYL ALCOHOL
FRAGRANCE
GLUTAMIC ACID
BIS-AMINOPROPYL DIMETHICONE
BENZYL ALCOHOL
CITRIC ACID
DISODIUM EDTA
HISTIDINE
PANTHENOL
PANTHENYL ETHYL ETHER
METHYLCHLOROISOTHIAZOLINONE
METHYLISOTHIAZOLINONE Example 3 Testing on Hair—Salon Expert Evaluation The inventions (Formulas B, C, and D) were tested on the hair of the heads of human panelists or mannequins and their performance were compared to that of the bench or comparative formula Y in Table 2.

The formulas B and C and the comparative formula were each applied onto 5 mannequin heads globally after the hair was shampooed by detergent-based formulations and the invention formulas and the comparative formula were rinsed off the hair. The hair was evaluated by an expert stylist before and after drying the hair. Relevant wet and dry attributes were scored on a scale of 1-5 and the ratings were averaged for 5 mannequin applications and compared to the averages of the comparative formula. Both invention formulas B and C yielded more dry mass and volume than the comparative formula and the hair was more individualized. Ease of combing the hair treated with the invention formulas was identical to that for hair treated with the comparative formula. The treatment with formula C resulted in slightly smoother effects on hair compared to the comparative formula and treatment with formula B resulted in less smooth effects on hair compared to the comparative formula The invention formula D and the comparative formula were also applied to 10 human panelists' hair as half head treatments and their performances on the hair were evaluated by expert stylists. During the application of the products on hair, the invention formula was slightly more readily absorbed during application and imparted less on-surface effects, made the hair more supple and slightly less sticky during application. After rinsing the hair, while still in the wet state, the hair treated with the invention formula had more mass but was slightly less supple. In the dry state (after drying the hair), the hair treated with the invention formula had slightly more mass, was slightly less easy to comb through and slightly less individualized.

In summary, when the hair was still wet, the hair treated with the invention showed better scores on the attributes of volume, root lift, mass effect of wet hair, and weighed less on hair. In the dry state, the hair treated with the invention showed better scores on the attributes of volume, root lift, mass effect, and body.

It is to be understood that the foregoing describes preferred embodiments of the disclosure and that modifications may be made therein without departing from the spirit or scope of the disclosure as set forth in the claims.

What is claimed is:

1. A composition for conditioning hair, the composition comprising:
(a) from about 0.1% to about 2% by weight of 3-aminopropyltriethoxysilane (APTES);
(b) from about 0.03% to about 1% by weight of at least one hydrophobic silica aerogel particle chosen from silica silylate;
(c) a first organic acid;
(d) from about 0.1% to about 6% by weight of at least one cationic surfactant chosen from dimethylamine derivatives;
(e) a second organic acid;
(f) from about 2% to about 12% by weight of at least one fatty alcohol chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, and mixtures thereof;
(g) water; and
(h) optionally, from about 0.15% to about 3% by weight of at least one silicone compound other than the at least one silane compound and chosen from dimethicone, dimethicone copolymer, amino functional silicones comprising at least one primary, secondary or tertiary amine or a quaternary ammonium group, and mixtures thereof;
all weights being based on the total weight of the composition; and wherein the first organic acid and the second organic acid are chosen from tartaric acid, lactic acid, malic acid, maleic acid, oxalic acid, malonic acid, citric acid, aspartic acid, salicylic acid, benzoic acid, acetic acid, formic acid, and mixtures thereof; and the composition is free from cellulose-based polymers.

2. A composition for conditioning hair, the composition comprising:

(a) from about 0.1% to about 2% by weight of 3-aminopropyltriethoxysilane (APTES);

(b) from about 0.03% to about 1% by weight of at least one hydrophobic silica aerogel particle chosen from silica silylate;

(c) a first organic acid;

(d) from about 0.1% to about 6% by weight of at least one cationic surfactant chosen from dimethylamine derivatives;

(e) a second organic acid;

(f) from about 2% to about 12% by weight of at least one fatty alcohol chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, and mixtures thereof;

(g) water; and (h) optionally, from about 0.15% to about 3% by weight of at least one silicone compound other than the at least one silane compound and chosen from dimethicone, dimethicone copolymer, amino functional silicones comprising at least one primary, secondary or tertiary amine or a quaternary ammonium group, and mixtures thereof;

all weights being based on the total weight of the composition; and wherein the first organic acid and the second organic acid are chosen from tartaric acid, lactic acid, malic acid, maleic acid, oxalic acid, malonic acid, citric acid, aspartic acid, salicylic acid, benzoic acid, acetic acid, formic acid, and mixtures thereof; and the composition is free from acrylic polymers.

3. A composition for conditioning hair, the composition comprising:

(a) from about 0.1% to about 2% by weight of 3-aminopropyltriethoxysilane (APTES);

(b) from about 0.03% to about 1% by weight of at least one hydrophobic silica aerogel particle chosen from silica silylate;

(c) a first organic acid;

(d) from about 0.1% to about 6% by weight of at least one cationic surfactant chosen from dimethylamine derivatives;

(e) a second organic acid;

(f) from about 2% to about 12% by weight of at least one fatty alcohol chosen from cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, and mixtures thereof;

(g) water; and (h) optionally, from about 0.15% to about 3% by weight of at least one silicone compound other than the at least one silane compound and chosen from dimethicone, dimethicone copolymer, amino functional silicones comprising at least one primary, secondary or tertiary amine or a quaternary ammonium group, and mixtures thereof;

all weights being based on the total weight of the composition; and wherein the first organic acid and the second organic acid are chosen from tartaric acid, lactic acid, malic acid, maleic acid, oxalic acid, malonic acid, citric acid, aspartic acid, salicylic acid, benzoic acid, acetic acid, formic acid, and mixtures thereof; and the composition is free from cellulose-based polymers and acrylic polymers.

* * * * *